(12) United States Patent  (10) Patent No.: US 7,542,808 B1
Peterson et al.  (45) Date of Patent: Jun. 2, 2009

(54) LEAD AND CATHETER ASSEMBLY

(75) Inventors: Charles Peterson, Murrieta, CA (US); John Greenland, San Diego, CA (US); Gary Hague, Carlsbad, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 161 days.

(21) Appl. No.: 10/944,303

(22) Filed: Sep. 17, 2004

(51) Int. Cl.
*A61N 1/05* (2006.01)
(52) U.S. Cl. ........................ 607/125; 607/122
(58) Field of Classification Search ................ 607/122, 607/125; 600/374, 381
See application file for complete search history.

(56) References Cited

U.S. PATENT DOCUMENTS

| | | | |
|---|---|---|---|
| 5,423,772 A | 6/1995 | Lurie et al. |
| 5,549,581 A | 8/1996 | Lurie et al. |
| 5,643,231 A | 7/1997 | Lurie et al. |
| 5,722,963 A | 3/1998 | Lurie et al. |
| 5,846,229 A | 12/1998 | Berg |
| 5,873,842 A | 2/1999 | Brennen et al. |
| 5,911,715 A | 6/1999 | Berg et al. |
| 5,984,909 A | 11/1999 | Lurie et al. |
| 6,001,085 A | 12/1999 | Lurie et al. |
| 6,122,552 A | 9/2000 | Tockman et al. |
| 6,126,649 A | 10/2000 | VanTassel et al. |
| 6,132,417 A | 10/2000 | Kiesz |
| 6,277,107 B1 | 8/2001 | Lurie et al. |
| 6,428,489 B1 | 8/2002 | Jacobsen et al. |
| 6,445,958 B1 | 9/2002 | Machek et al. |
| 6,458,107 B1 | 10/2002 | Ockuly |
| 6,556,873 B1 | 4/2003 | Smits |
| 6,610,058 B2 | 8/2003 | Flores |
| 6,612,999 B2 | 9/2003 | Brennan et al. |
| 6,638,268 B2 | 10/2003 | Niazi |
| 6,656,166 B2 | 12/2003 | Lurie et al. |
| 6,697,667 B1 | 2/2004 | Lee et al. |
| 6,704,590 B2 | 3/2004 | Haldeman |
| 6,741,893 B2 | 5/2004 | Smits |
| 6,758,854 B1 | 7/2004 | Butler et al. |
| 2003/0028153 A1 | 2/2003 | Brennan et al. |
| 2003/0060802 A1 | 3/2003 | Omaleki et al. |
| 2003/0144657 A1 | 7/2003 | Bowe et al. |
| 2003/0195525 A1 | 10/2003 | Peterson et al. |
| 2003/0208141 A1 | 11/2003 | Worley et al. |
| 2003/0208220 A1 | 11/2003 | Worley et al. |
| 2004/0019359 A1 | 1/2004 | Worley et al. |
| 2004/0092844 A1 | 5/2004 | Johnson et al. |
| 2004/0102830 A1 | 5/2004 | Williams |
| 2004/0116849 A1 | 6/2004 | Gardeski |

(Continued)

*Primary Examiner*—Carl H Layno
*Assistant Examiner*—Yun Haeng Lee
(74) *Attorney, Agent, or Firm*—Faegre & Benson LLP

(57) ABSTRACT

A guide catheter assembly for accessing lateral branch veins of the coronary sinus includes a guide catheter and a pacing lead. The guide catheter has a central lumen therethrough, a proximal end and a distal end pre-formed with a guide curve. The pacing lead is slidably receivable within the guide catheter lumen. The pacing lead has a proximal end and a distal end formed with a first curve and a second curve extending proximally from the first curve. The second curve is adapted to mate with the guide curve to direct the first curve into a selected branch vein of the coronary sinus. The second curve may be pre-formed in the pacing lead, or may be imparted to the pacing lead via a stylet or inner catheter.

24 Claims, 15 Drawing Sheets

U.S. PATENT DOCUMENTS

2004/0116993 A1 6/2004 Clemens et al.
2004/0176688 A1 9/2004 Haldeman
2004/0220520 A1 11/2004 Simpson et al.

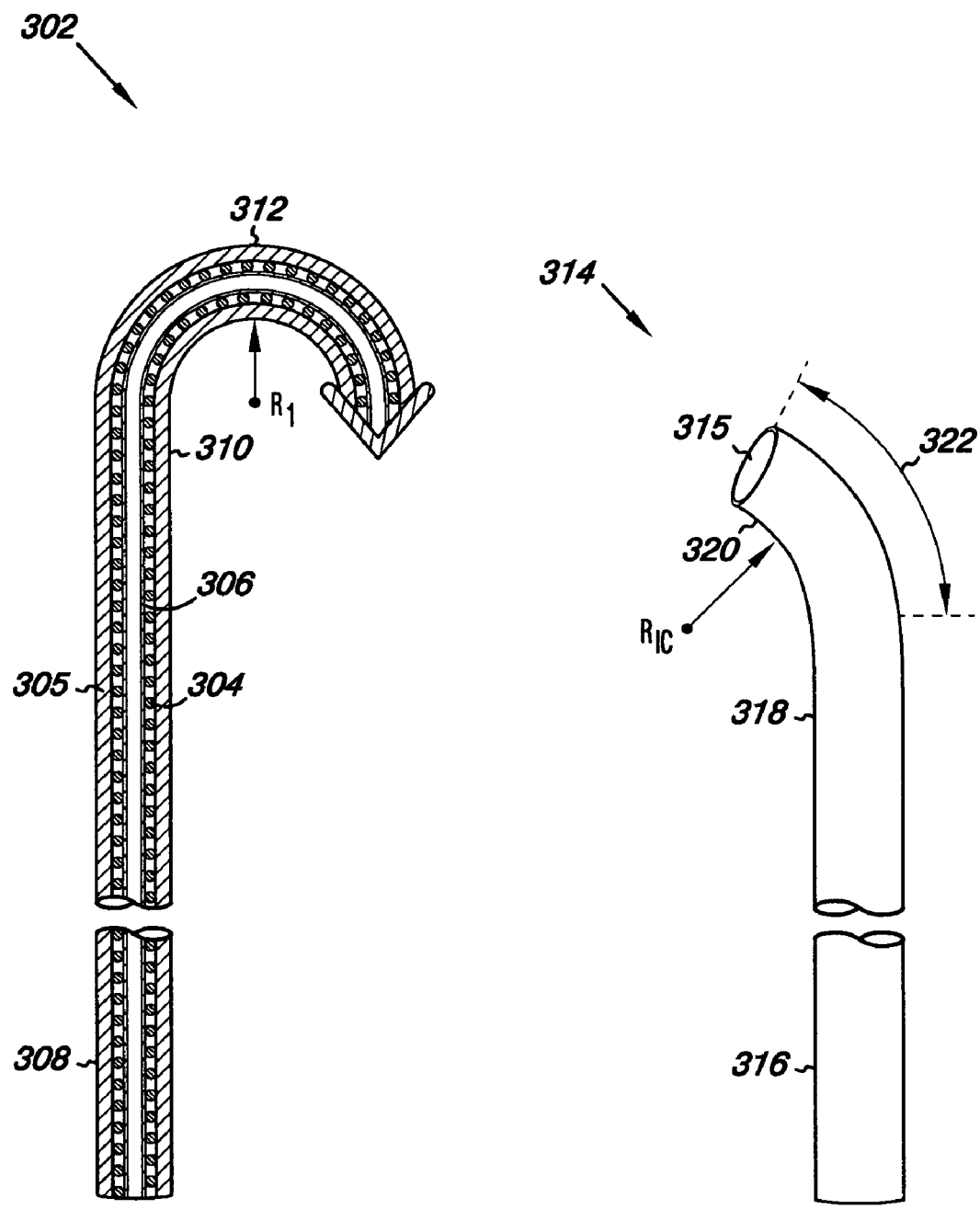
*Fig. 9A*  *Fig. 9B*

LEAD AND CATHETER ASSEMBLY

FIELD OF THE INVENTION

The present invention relates to cardiovascular leads and catheters and methods of using the leads and catheters. More specifically, it relates to a lead and catheter assembly for accessing branch vessels of the coronary sinus.

BACKGROUND

Guide catheter assemblies are employed as conduits for delivery of payloads such as cardiac pacing leads into the vasculature. Guide catheter assemblies typically include a flexible lead slidably received in a somewhat less flexible guide catheter. The distal ends of such leads are sometimes pre-formed with a curvature adapted to facilitate access of particular anatomic features, for example, lateral branch veins of the coronary sinus. However, pacing leads are typically of a length and flexibility such that the distal end of the lead exhibits little or no torque response to torqueing forces applied to the proximal end of the lead. It can be difficult to properly align the distal end of the lead to the branch veins so as to take advantage of the distal curvature of the lead.

There is a need in the art for a device and method for aligning the distal end of a pacing lead with desired anatomical features.

BRIEF SUMMARY OF THE INVENTION

The present invention, in one embodiment, is a lead and catheter assembly for accessing lateral branch veins of the coronary sinus. The lead and catheter assembly includes a guide catheter and a pacing lead. The guide catheter has an open lumen extending therethrough, a proximal end and a distal end pre-formed with a guide curve. The pacing lead is slidably receivable within the guide catheter lumen. The pacing lead has a proximal end and a distal end. The distal end is formed with a first curve and a second curve extending proximally from the first curve. The second curve is adapted to mate with the guide curve to direct the first curve into a selected branch of the coronary sinus. According to one embodiment, the first curve extends through an angle of from about 70° to about 270° in the opposite direction as the second curve. According to one embodiment, the second curve is formed with a stylet. According to yet another embodiment, the second curve is formed with an inner catheter.

The present invention, in another embodiment, is a pacing lead and catheter assembly for accessing lateral branch veins of the coronary sinus. The pacing lead and catheter assembly includes a guide catheter having an open lumen extending therethrough, a proximal end and a distal end. The distal end is pre-formed with a guide curve. A pacing lead is slidably receivable within the guide catheter lumen and has a proximal end and a distal end. The distal end is formed with a first curve extending through an angle of from about 70° to about 270°. The lead and catheter assembly further includes alignment means for imparting a second curve to the pacing lead corresponding to the guide curve and adapted to mate with the guide curve to direct the first curve into a selected branch vessel of the coronary sinus.

The present invention, according to another embodiment, is a method of accessing lateral branch veins of the coronary sinus with a pacing lead and guide catheter assembly. The guide catheter has an open lumen extending therethrough and a distal end provided with a pre-formed guide curve. The pacing lead has a distal end provided with a first curve and a second curve extending proximally from the first curve. The guide catheter is inserted into an access vessel to the heart. The guide catheter is advanced along the access vessel to the coronary sinus. The pacing lead is inserted into the guide catheter lumen. The pacing lead is advanced distally through the guide catheter. The second curve of the pacing lead is advanced through the guide curve. The pacing lead is allowed to rotate as the second curve aligns with the guide curve. The first curve of the pacing lead is advanced into the lateral branch of the coronary sinus. According to one embodiment, the lead is pre-formed with the first curve and the second curve. According to another embodiment, a stylet is inserted into the lead to form the second curve. According to yet another embodiment, the lead is inserted into an inner catheter to form the second curve.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 9A is a sectional view of a pacing lead according to another embodiment of the present invention.

FIG. 9B is a sectional view of an inner catheter for use with the pacing lead of FIG. 9A.

DETAILED DESCRIPTION

Figure 1:
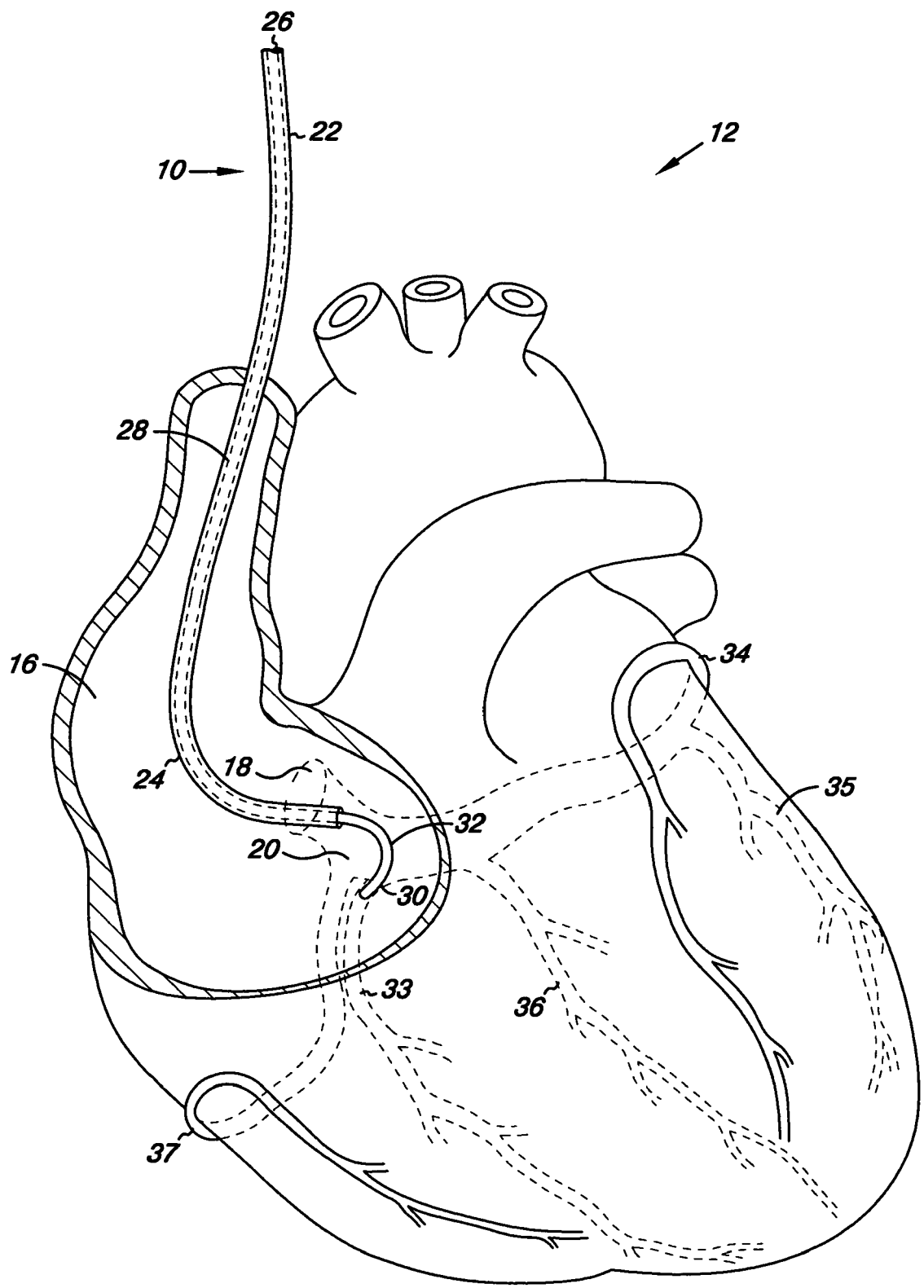
FIG. 1 is a sectional view of a pacing lead and catheter assembly and a portion of the vasculature according to one embodiment of the present invention.

FIG. 1 is a perspective view of a pacing lead and catheter assembly 10 accessing a heart 12 via the right atrium 16. The lead and catheter assembly 10 extends into the right atrium 16, through the coronary sinus ostium 18 and into the coronary sinus 20. The lead and catheter assembly 10 includes a guide catheter 22 having a pre-formed guide curve 24 adapted to facilitate access to the coronary sinus 20. The guide curve 24 is generally shaped like a "J" and may be made up of a single or multiple curved segments. The guide catheter 22 also has a central open lumen 26 for slidably receiving a pacing lead 28. The guide catheter 22 serves as a conduit for delivery of a distal end 30 of the pacing lead 28 into the coronary sinus 20. The distal end 30 of the pacing lead 28 is pre-formed with a first or distal curve 32 adapted for facilitating access of a branch vein of the coronary sinus 20, such as the middle cardiac vein 33.

Once positioned in the middle cardiac vein 33, the pacing lead 28 can be used to sense the electrical activity of the heart 12 or to apply a stimulating pulse to the heart 12. In other embodiments, the lead and catheter assembly 10 is operable to access any other branch vein of the coronary sinus 20 as is known in the art of cardiac function management. For example, it may be used to access the great cardiac vein 34, the left marginal vein 35, the left posterior ventricular vein 36 or the small cardiac vein 37.

Figure 2:
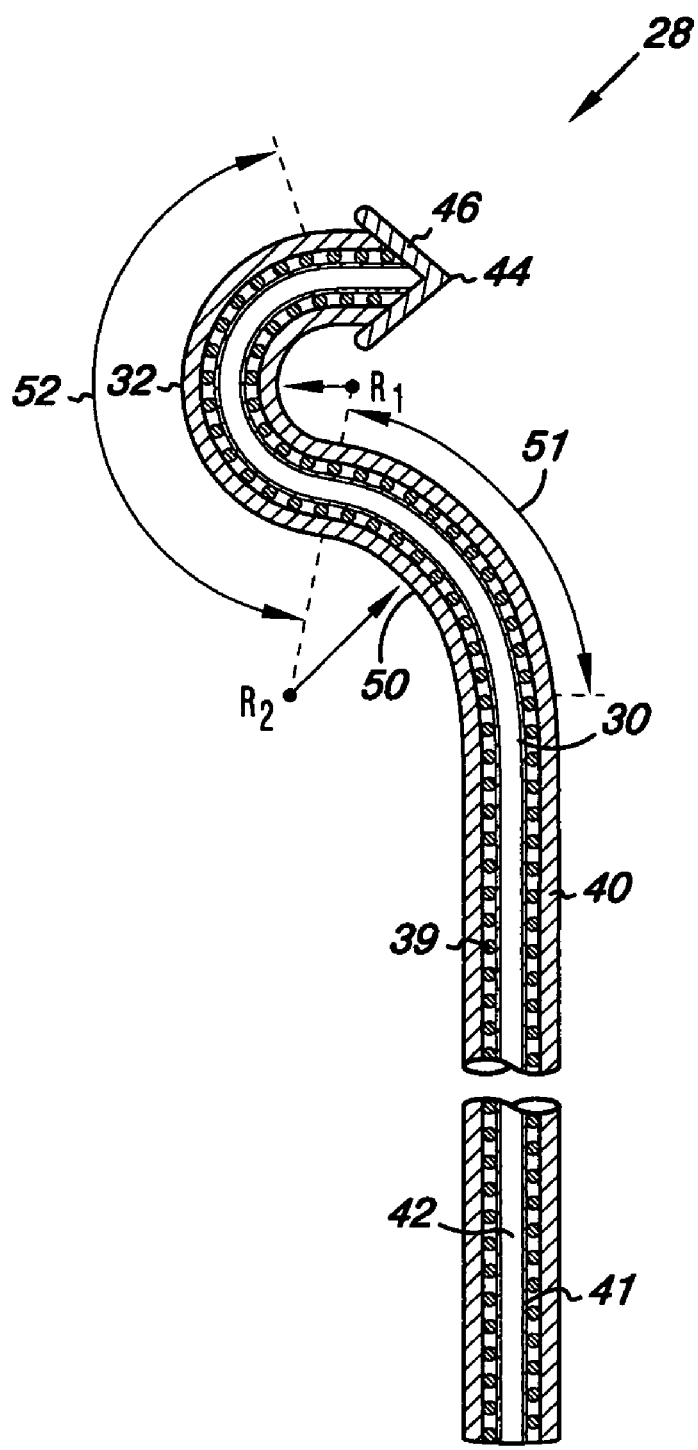
FIG. 2 is a sectional view of a pacing lead according to one embodiment of the present invention.

FIG. 2 is a detailed sectional view of a pacing lead 28 according to one embodiment of the present invention. The pacing lead 28 is an elongated flexible member constructed of an inner conductive coil 39 sandwiched between an outer sheath 40 and an inner sheath 41. According to one embodiment, the pacing lead 28 has an overall length of from about 65 cm to about 110 cm. According to another embodiment, the pacing lead 28 has an overall length of from about 80 cm to about 100 cm. The pacing lead 28 has a generally straight or unbiased proximal end 42 and a curved or biased distal end 30. The proximal end 42 is operable to manipulate the distal end 30 through the guide catheter 22 and to position a tip 44 of the distal end 30 into a branch vein of the coronary sinus 20 (as positioned in FIG. 1). According to one embodiment, a fixation mechanism 46 is coupled to the distal tip 44. Fixation mechanism 46 assists in securing the distal tip 44 of the lead 28 into a chosen branch vessel.

According to one embodiment, the distal end 30 of the lead 28 is pre-formed with a first or distal curve 32 and a second or proximal curve 50 extending proximally from the distal curve 32. As further explained below, the proximal curve 50 is configured to direct the distal end 30 of the lead 28 into the coronary sinus 20, while the distal curve 32 is configured to direct the tip 44 toward a desired branch vessel. The particular shapes of the curves 32, 50 will vary based upon the patient's anatomy and the branch vessel to be accessed.

The proximal curve 50 is configured to facilitate access to the coronary sinus 20. According to one embodiment, the proximal curve 50 extends from about 15° to about 180° relative to the proximal end 42 of the lead 28, as indicated by arrow 51. According to another embodiment, the proximal curve 50 extends about 60° relative to the proximal end 42 of the lead 28. According to another embodiment, the proximal curve 50 has a curvature generally similar to that of the guide catheter curve 24 (See FIG. 1). The distal curve 32 is generally configured to facilitate access to branch veins of the coronary sinus 20. The distal curve 32 may have a variety of configurations in order to facilitate access to particular branch veins, or to accommodate unusual patient heart physiology due to disease or other abnormality. According to one embodiment, the distal curve 32 extends from about 70° to about 270° in the reverse direction as the proximal curve 50, as shown by arrow 52. According to another embodiment, the distal curve 32 extends about 150° in the reverse direction as the proximal curve 50. According to one embodiment, the distal curve 32 extends tangent to the proximal curve 50 and in the same plane as the proximal curve 50.

The distal curve 32 has a radius of curvature $R_1$ of at most about half a radius of curvature $R_2$ of the proximal curve 50. The radius of curvature $R_1$ of the distal curve 32 and the radius of curvature $R_2$ of the proximal curve 50 may be sized up or down as appropriate to a particular patient's physiology. For example, according to one embodiment, the radius of curvature $R_1$ of the distal curve 32 is from about 1 cm to about 7.5 cm and the radius of curvature $R_2$ of the proximal curve 50 is from about 2 cm to about 15 cm.

According to one embodiment, the distal curve 32 and proximal curve 50 are pre-formed in the lead 28. The lead 28 may be pre-formed with the curves 32, 50 according to any means known in the art. For example, in one embodiment, the lead 28 is heat-set to form curves 32 and 50. According to another embodiment, lead 28 is plastically deformed to form curves 32, 50. For example, lead 28 may be packaged in the desired curved configuration. After residing in the packaging for a sufficient period of time, the lead 28 retains the curved configuration imparted by the packaging following removal from the packaging. According to another example, a temporary shaped stylet is pre-loaded into the lead 28 to form the curves 32 and 50 prior to packaging. After a sufficient period of time, the lead 28 retains the curvature imparted by the stylet following removal of the stylet prior to an insertion procedure. According to other embodiments, a combination of methods of forming the lead 28 with curves 32, 50 may be employed. For example, distal curve 32 may be heat-set into the lead 28, while proximal curve 50 is formed in the lead 28 via packaging materials and/or the insertion of a temporary stylet.

According to one embodiment, certain portions of the lead 28 may have increased stiffness or resistance to bending. In one example, the portion of the lead 28 forming proximal curve 50 has an increased stiffness relative to the remainder of the lead 28. The stiffer portion of the lead 28 is more readily plastically deformed into the curvature imparted by packaging materials or a temporary stylet.

Figure 3A:
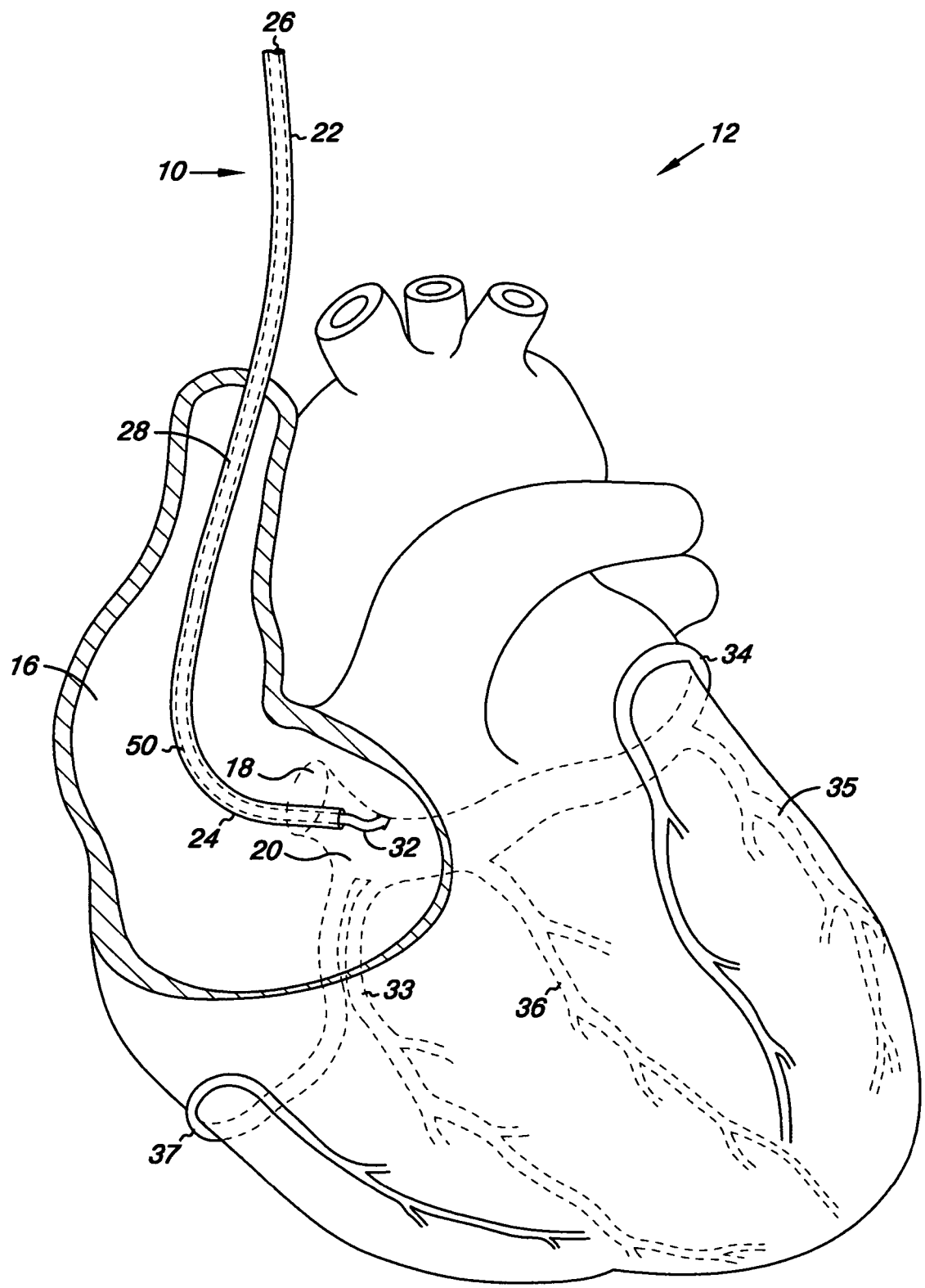
FIG. 3A is a sectional view of a lead and catheter assembly and a portion of the vasculature according to one embodiment of the present invention, in which the pacing lead is advanced to a first position with respect the guide catheter.
Figure 3B:
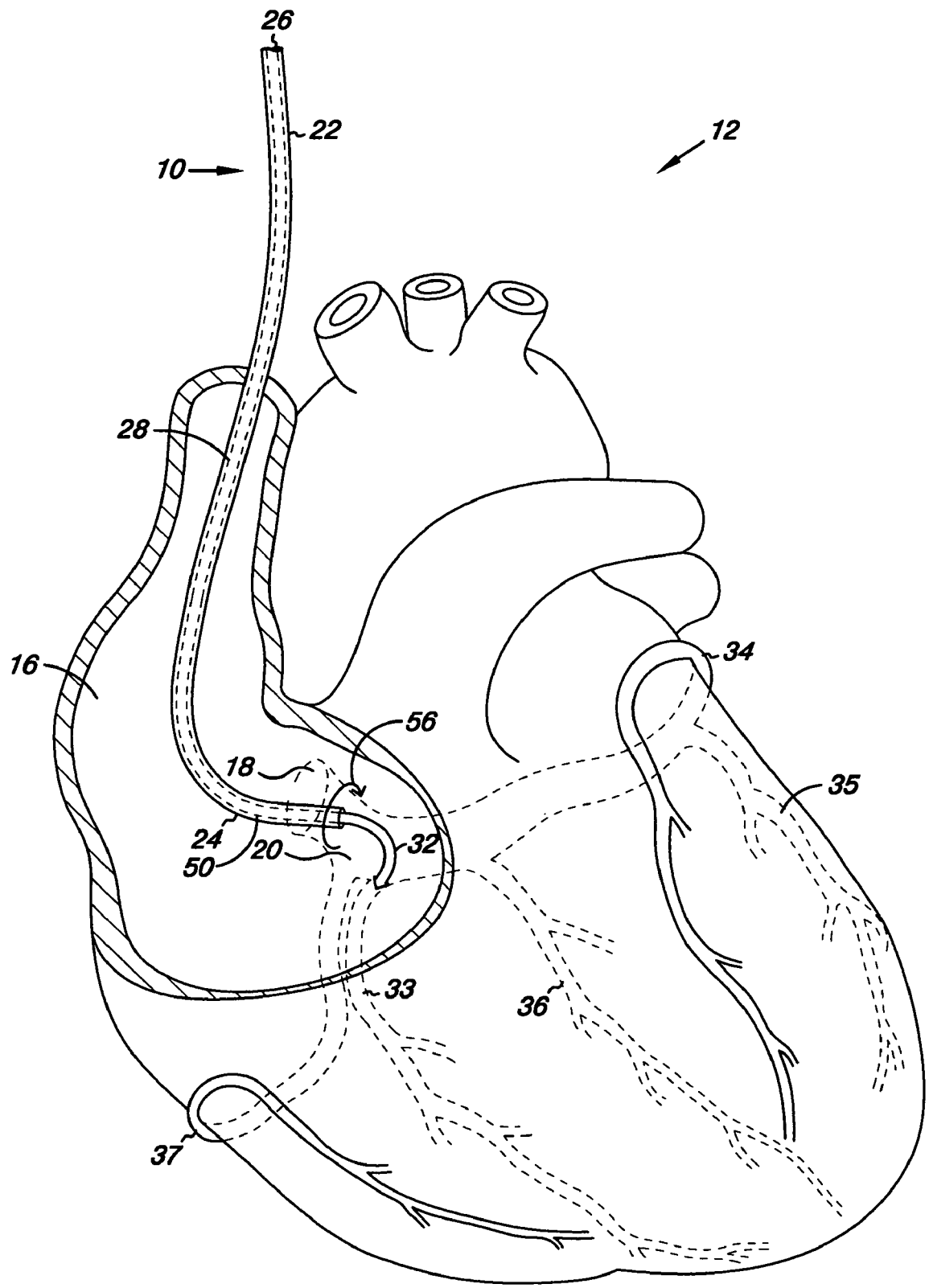
FIG. 3B is a sectional view of the lead and catheter assembly and the portion of the vasculature of FIG. 3A in which the pacing lead is advanced to a second position with respect to the guide catheter.

FIGS. 3A and 3B show the pacing lead and catheter assembly 10 of FIG. 2 at various stages in an implantation procedure. FIG. 3A shows the pacing lead 28 inserted into a guide catheter 22 as previously described. As the lead distal curve 32 traverses the guide catheter curve 24, the distal curve 32 tends to become generally aligned with the guide catheter curve 24 towards the coronary sinus 20. However, as shown in FIG. 3A, the lateral branches 33, 34, 35, 36 and 37 of the coronary sinus 20 curve in different directions as the curve into the coronary sinus ostium 18 from the right atrium 16. In general, then, pacing leads such as pacing lead 28 having a distal curve 32 for facilitating access to the lateral branch veins of the coronary sinus 20 will align to the guide catheter curve 24 as the distal curve 32 traverses the guide catheter curve 24. As a result, the lead distal curve 32 often becomes mis-aligned with respect to the curvature of the lateral branch veins by up to about 180°. In such a situation, as shown in FIG. 3A, the distal curve 32 is not positioned to access branch veins.

FIG. 3B shows the pacing lead 28 distally advanced within the guide catheter 22 such that the proximal curve 50 has partially traversed the guide catheter curve 24. As the proximal curve 50 continues to traverse the guide catheter curve 24, the proximal curve 50 tends to mate with or become generally aligned with the guide catheter curve 24. In doing so, the lead 28 rotates, as shown by arrows 56. The distal curve 32 becomes aligned to the lateral branch vessels to facilitate access. According to one embodiment, the lead 28 is positioned to take advantage of the shape of the distal curve 32 to facilitate access to the middle cardiac vein 33. The position or alignment of the distal curve 32 of the lead 28 is dependent in part on the relationship between the distal curve 32 and the proximal curve 50. In general, the distal curve 32 may be formed relative to the proximal curve 50 such that the distal curve 32 is aligned to a pre-chosen plane within the coronary sinus 20 when the proximal curve 50 is aligned or mated with the guide catheter curve 24.

In general, leads are designed with very little torque response at the distal end when twisted or torqued at the proximal end. The lead 28 in accordance with the present embodiment self-orients the distal curve 32 in a pre-chosen plane. Orientation occurs as the proximal curve 50 aligns to the guide catheter curve 24, causing the distal curve 32 to align to a pre-chosen plane with respect to the guide catheter curve 24 and the proximal curve 50. It is not necessary for the physician to attempt to torque or steer the proximal end 42 (not shown) in order to align the distal curve 32 with the chosen lateral branch veins of the coronary sinus 20. The pacing lead 28 may be reliably positioned to make efficient use of the distal curve 32 to access the lateral branch veins of the coronary sinus 20.

Figure 4:
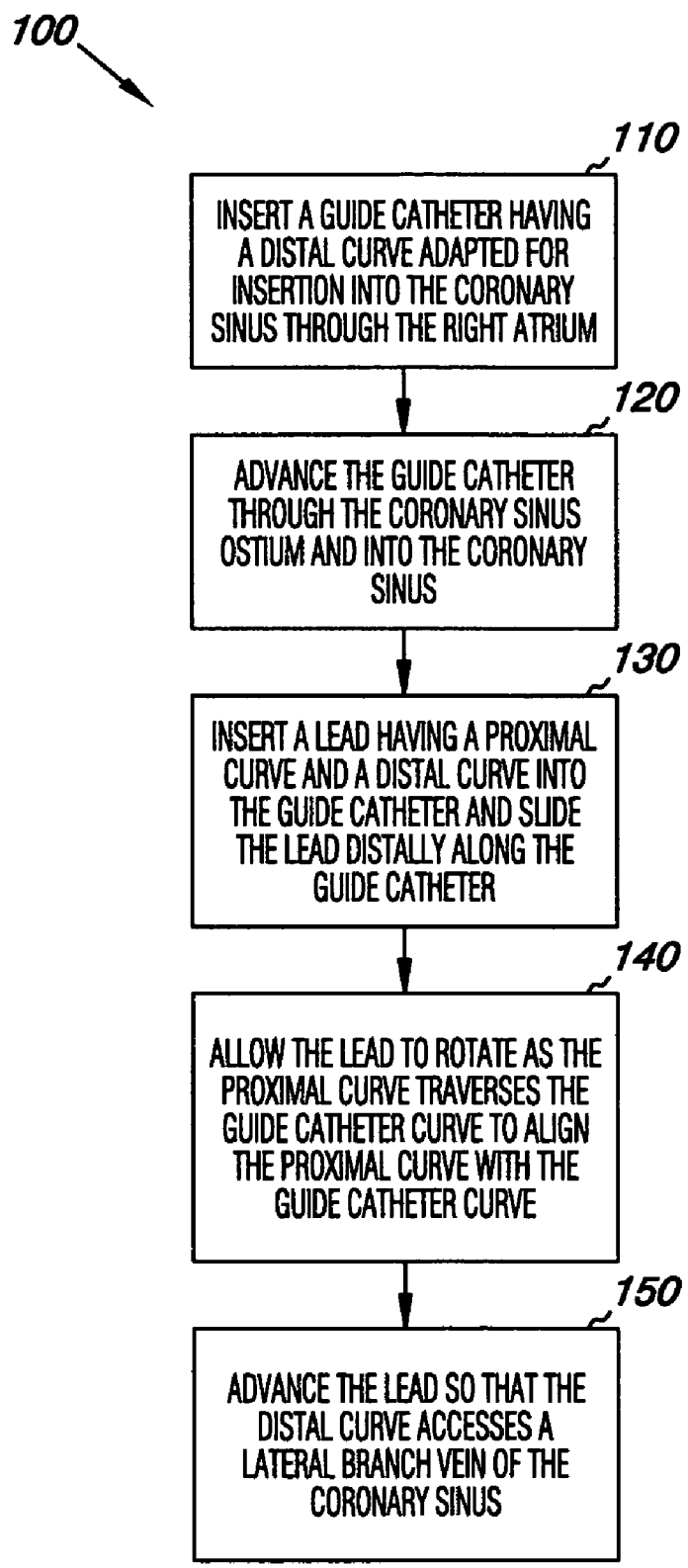
FIG. 4 is a flowchart depicting a method of accessing branch veins of the coronary sinus according to one embodiment of the present invention.

FIG. 4 is a flowchart showing a method 100 of accessing a lateral branch vein of the coronary sinus in accordance with one embodiment of the present invention. A guide catheter having a distal curve adapted for insertion into the coronary sinus is inserted into the right atrium (block 110). The guide catheter is advanced through the coronary sinus ostium and into the coronary sinus (block 120). A lead having a proximal curve and a distal curve in accordance with the present invention is inserted into the guide catheter and slid distally along the guide catheter lumen (block 130). The lead is allowed to rotate as the proximal curve traverses the guide catheter curve to align the proximal curve with the guide catheter curve (block 140). The lead is advanced so that the distal curve accesses a lateral branch vein of the coronary sinus (block 150).

Figure 5:
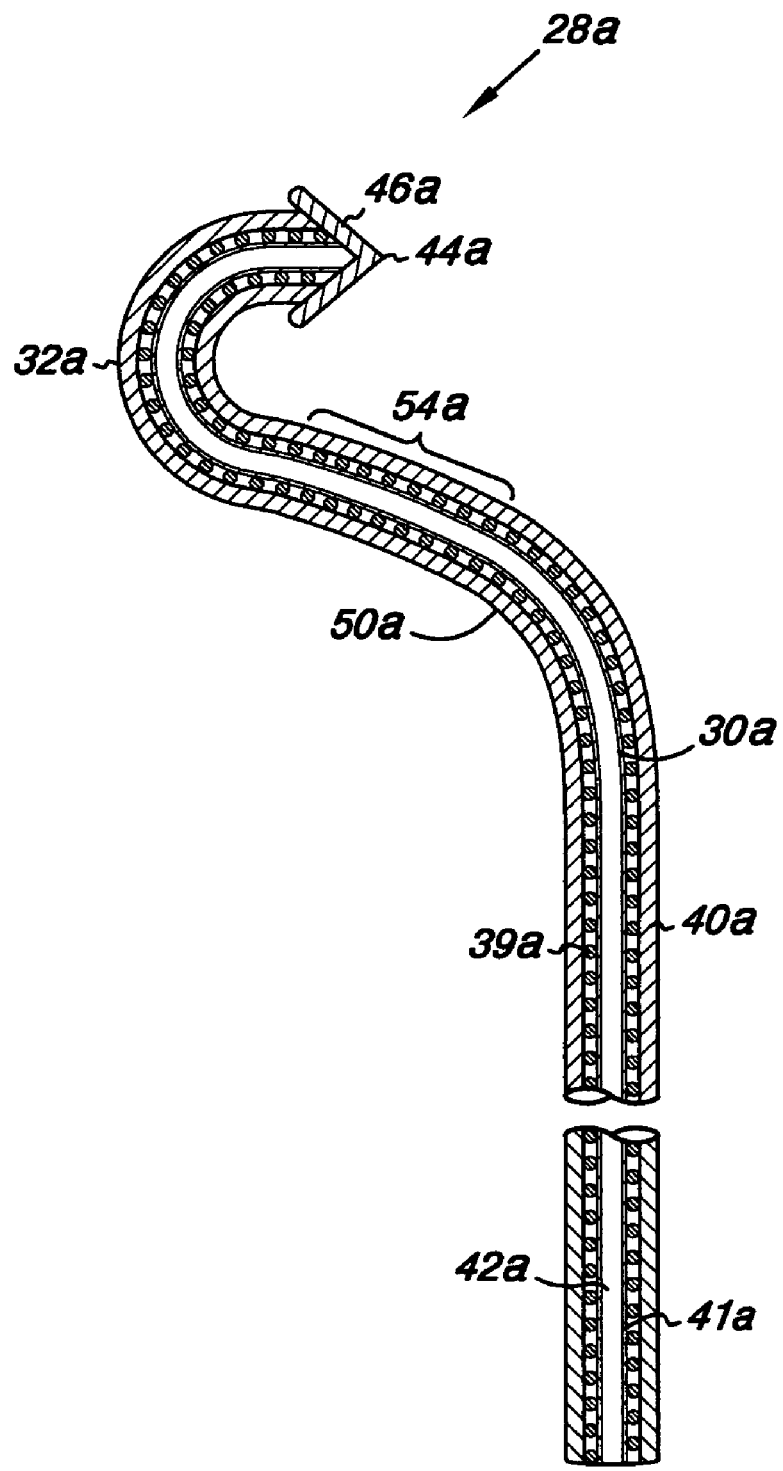
FIG. 5 is a sectional view of a pacing lead according to another embodiment of the present invention.

FIG. 5 shows a pacing lead 28a in accordance with another embodiment of the present invention. The lead 28a of FIG. 5 is generally similar to the lead 28 shown in FIG. 2. However, the distal curve 32a is separated from the proximal curve 50a by a generally straight intermediate segment 54a. According to one embodiment, intermediate segment 54a has a length of from about 1 cm to about 2 cm. Intermediate segment 54a is useful in facilitating access to branch veins positioned somewhat further from the coronary sinus ostium 18, such as the great cardiac vein 34 and the left marginal vein 35. Due to the separation between the distal curve 32a and the proximal curve 50a, the distal curve 32a will tend to advance further into the coronary sinus 20 prior to rotating into alignment as the proximal curve 50a traverses the guide catheter curve 24. A delayed alignment may be helpful in preventing inadvertent access of branch vessels, or to accommodate unusual patient physiology. According to another embodiment, the distal curve 32a is spaced apart from the proximal curve 50a a distance chosen to enhance access of the distal curve 32a into a selected branch vessel of the coronary sinus 20.

Figure 6:
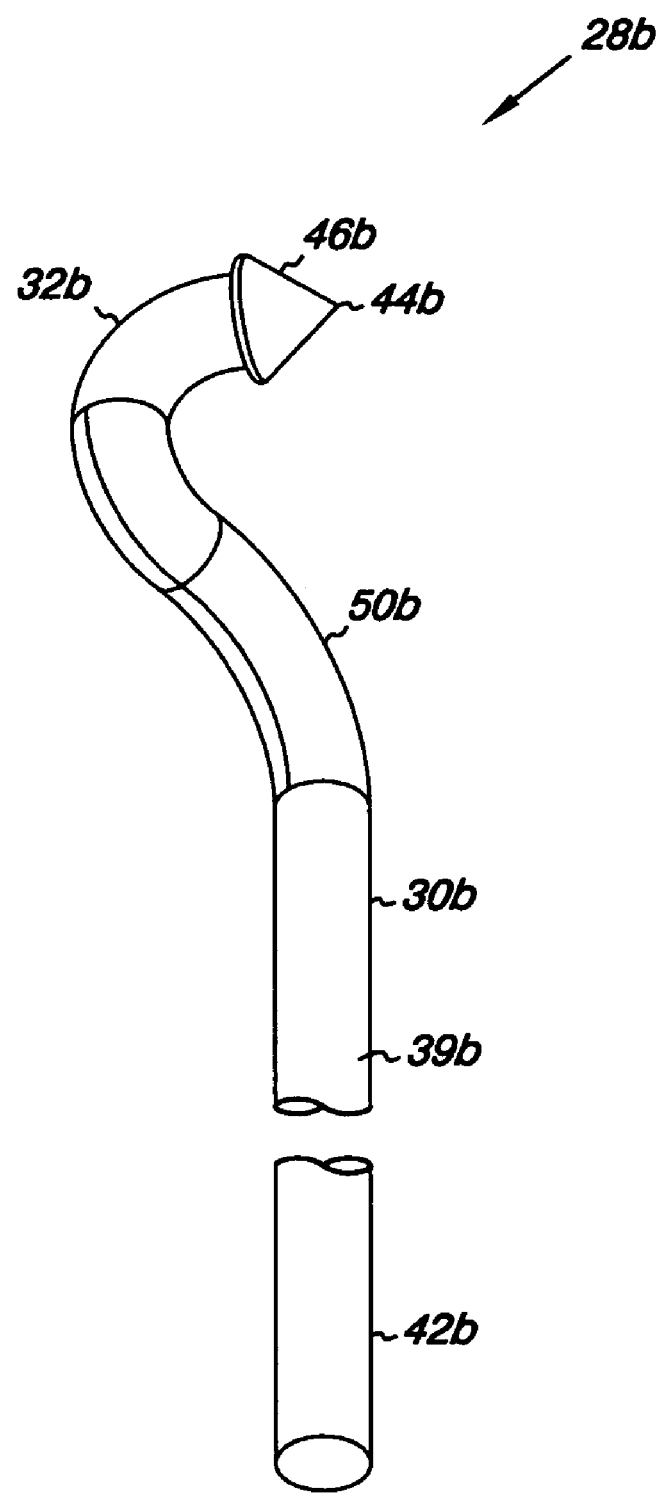
FIG. 6 is a perspective view of a pacing lead according to yet another embodiment of the present invention.

FIG. 6 shows a pacing lead 28b in accordance with another embodiment of the present invention. The lead 28b of FIG. 6 is generally similar to the lead 28 shown in FIG. 2. However, the distal curve 32b extends through a different plane than the proximal curve 50b. According to one embodiment, the distal curve 32b extends up to about 60° out-of-plane with respect to the proximal curve 50b. An out-of-plane proximal curve 32b may be useful for accessing branch vessels having unusual take-off angles.

Figures 7A, 7B:
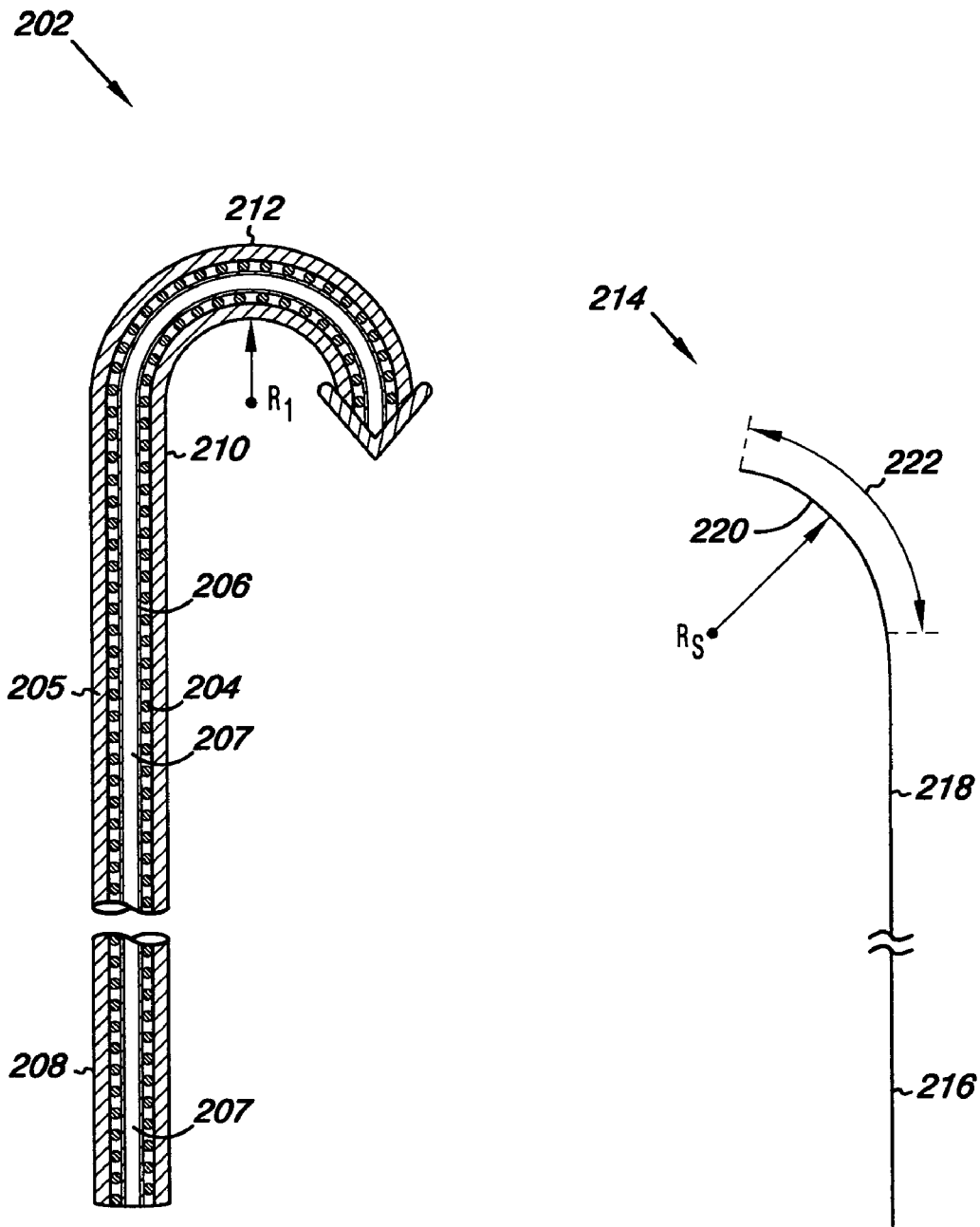
FIG. 7A is a sectional view of a pacing lead according to another embodiment of the present invention.
FIG. 7B is a side view of a stylet for use with the pacing lead of FIG. 7A.

FIGS. 7A-7D show a pacing lead and stylet assembly 200 according to another embodiment of the present invention, in which a portion of the lead curvature is formed with a stylet. FIG. 7A shows a side sectional view of a lead 202 in accordance with one embodiment of the present invention. Lead 202 is an elongated flexible member constructed of an inner conductive coil 204 sandwiched between an outer sheath 205 and an inner sheath 206. Lead 202 is provided with a longitudinally extending inner lumen 207. A proximal end 208 of the lead 202 is generally straight or unbiased and is operable to manipulate a curved or biased distal end 210 of the lead 202 to gain access to lateral branch veins of the coronary sinus 20. The distal end 210 is provided with a pre-formed distal curve 212 having a radius of curvature $R_1$ shaped to facilitate such access.

FIG. 7B shows a side view of a stylet 214 for use in combination with the lead 202 of FIG. 7A. The stylet 214 is an elongated rigid member having a generally straight proximal portion 216 and a distal portion 218 provided with a pre-formed curve 220. The stylet 214 is sized to be received in the lead lumen 207 to provide support and shape to the lead 202 as the lead 202 is advanced within a guide catheter. According to one embodiment, the stylet curve 220 has a radius of curvature $R_S$ of at least about twice the radius of curvature $R_1$ of the lead distal curve 212. According to one embodiment, the stylet radius of curvature $R_S$ is from about 2 cm to about 15 cm and the lead radius of curvature $R_1$ is from about 1 cm to about 7.5 cm. According to one embodiment, the stylet curve 220 extends from about 15° to about 180° relative to the proximal portion 216 of the stylet 214, as indicated by arrow 222. According to another embodiment, the stylet curve 220 extends about 60° relative to the proximal portion 216 of the stylet 214.

Figure 7C:
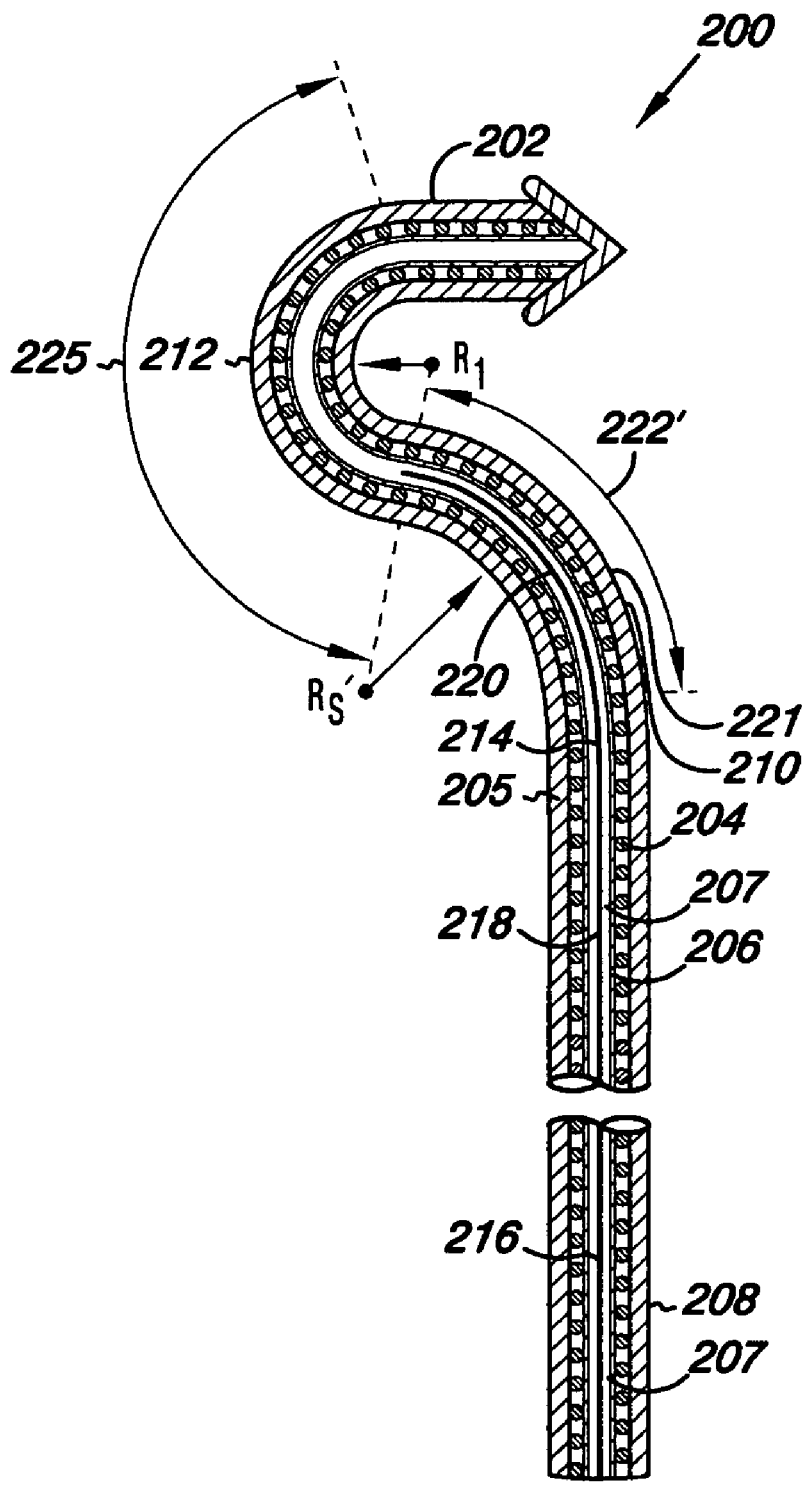
FIG. 7C is a sectional view of the pacing lead of FIG. 7A assembled with the stylet of FIG. 7B.

FIG. 7C shows a side sectional view of a pacing lead and stylet assembly 200 in which the stylet 214 of FIG. 7B is inserted into the lead lumen 207 of the lead 202 of FIG. 7A. The stylet 214 is positioned in the lead lumen 207 so that the stylet curve 220 is proximal to the lead distal curve 212. The stylet 214 is sufficiently rigid to cause the lead 202 to bend in conformity with the stylet curve 220. The lead 202 is thereby provided with a stylet-induced or proximal curve 221 in addition to the distal curve 212. The proximal curve 221 has a radius of curvature $R_S'$ about the same as the radius of curvature $R_S$ of the stylet curve 220. The proximal curve 221 also extends relative to the proximal portion 208 of the lead 202, as shown by arrow 222', as the stylet curve 220 extends with respect to the proximal portion 216 of the stylet 214.

According to one embodiment, the lead proximal curve 221 extends from about 15° to about 180° relative to the proximal portion 208 of the lead 202, as indicated by arrow 222'. According to another embodiment, the lead proximal curve 221 extends about 60° relative to the proximal portion 208 of the lead 202. According to one embodiment, the stylet 214 is positioned in the lead lumen 207 so that the lead distal curve 212 extends from about 70° to about 270° in the reverse direction as the lead proximal curve 221, as shown by arrow 225. According to another embodiment, the stylet 214 is positioned in the lead lumen 207 so that the lead distal curve 212 extends about 150° in the reverse direction as the lead proximal curve 221. According to one embodiment, the radius of curvature $R_S'$ of the lead proximal curve 321 is at least about twice the radius of curvature $R_1$ of the lead distal curve 212. According to one embodiment, the radius of curvature $R_S'$ of the lead proximal curve 321 is from about 2 cm to about 15 cm and the radius of curvature $R_1$ of the lead distal curve 212 is from about 1 cm to about 7.5 cm.

FIG. 7C shows stylet 214 advanced within the lead lumen 207 to a position relative to the lead distal curve 212 such that the distal curve 212 extends tangent to the stylet-induced or proximal curve 221. However, it is contemplated that in other embodiments, the stylet 214 may be positioned such that the proximal curve 221 is spaced apart from the lead distal curve 212 by from about 1 cm to about 2 cm.

FIG. 7C shows the stylet 214 of FIG. 7B positioned within the lead lumen 207 such that the lead distal curve 212 extends in the same plane as the lead proximal curve 221. However, according to other embodiments, it is contemplated that the stylet 214 may be positioned such that the lead distal curve 212 extends up to about 60° out-of-plane with respect to the lead proximal curve 221. An out-of-plane lead distal curve 212 would be useful for accessing vessels having unusual take-off angles.

Figure 7D:
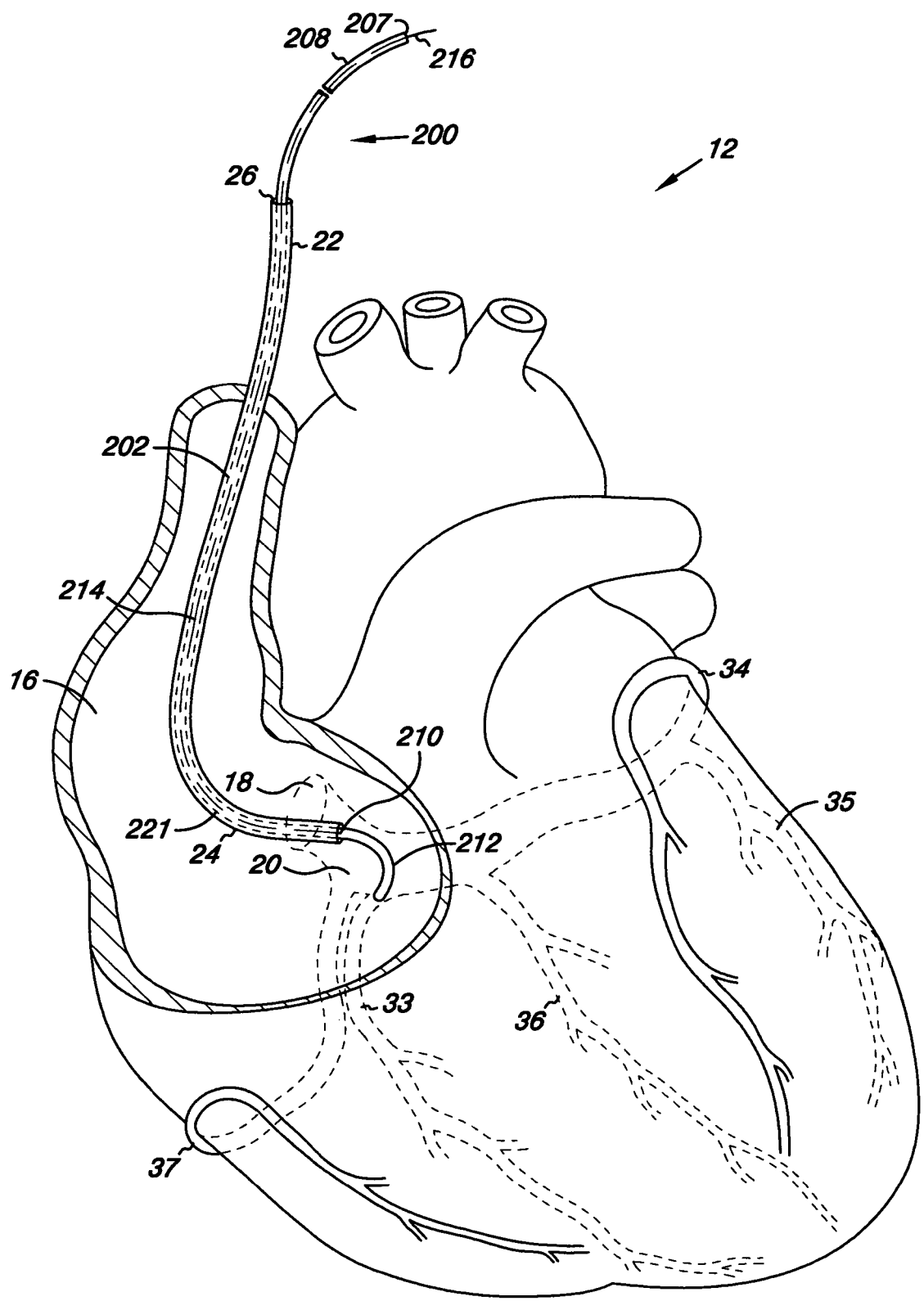
FIG. 7D is a sectional view of the pacing lead and stylet assembly of FIG. 7C inserted into a portion of the vasculature.

FIG. 7D shows the pacing lead and stylet assembly 200 of FIG. 7C and a portion of the vasculature. The lead assembly 200 is shown employed in combination with a guide catheter 22 as previously described. The lead and stylet assembly 200 is slidably received in guide catheter lumen 26. The stylet-induced or proximal curve 221 aligns with the guide catheter curve 24 as the lead and stylet assembly 200 advances distally through the guide catheter lumen 26. The distal curve 212 is thus aligned to a pre-chosen plane, in this case aligned to access the middle cardiac vein 33. According to other embodiments, the lead and stylet assembly 200 may be employed to access any other lateral branch vein of the coronary sinus 20 as is known in the art of cardiac function management. For example, the lead and stylet assembly 200 may be employed to access the great cardiac vein 34, the left marginal vein 35, the left posterior ventricular vein 36 or the small cardiac vein 37.

Figure 8:
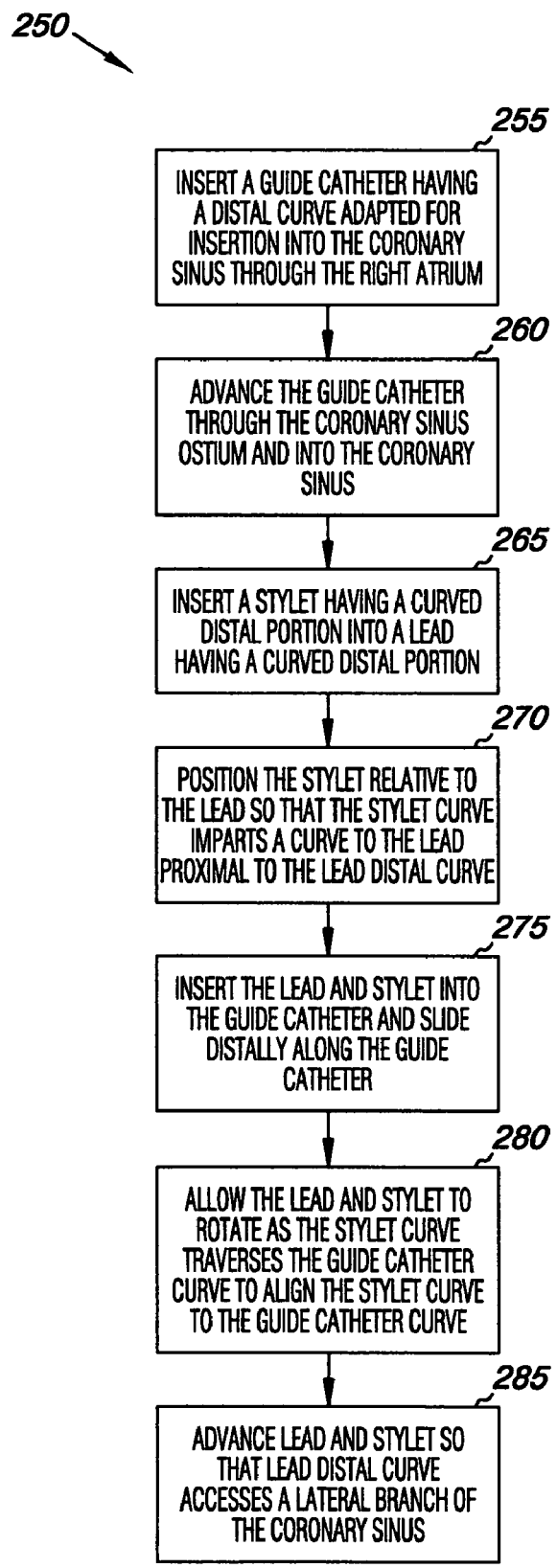
FIG. 8 is a flowchart depicting a method of accessing lateral branch veins of the coronary sinus according to one embodiment of the present invention.

FIG. 8 is a flowchart depicting a method 250 of accessing lateral branch veins of the coronary sinus according to one embodiment of the present invention. A guide catheter having a distal curve adapted for insertion into the coronary sinus is inserted into the right atrium (block 255). The guide catheter is advanced through the coronary sinus ostium and into the coronary sinus (block 260). A stylet having a curved distal portion is inserted into the lumen of a lead having a curved distal portion (block 265). The stylet is positioned relative to the lead so that the stylet curve imparts a curve to the lead proximal to the lead distal curve (block 270). The lead and stylet are inserted into the guide catheter and slid distally along the guide catheter (block 275). The lead and stylet are allowed to rotate as the stylet curve traverses the guide catheter curve to align the stylet curve with the guide catheter curve (block 280). The lead and stylet are advanced so that the lead distal curve accesses a lateral branch vein of the coronary sinus (block 285).

Figure 9C:
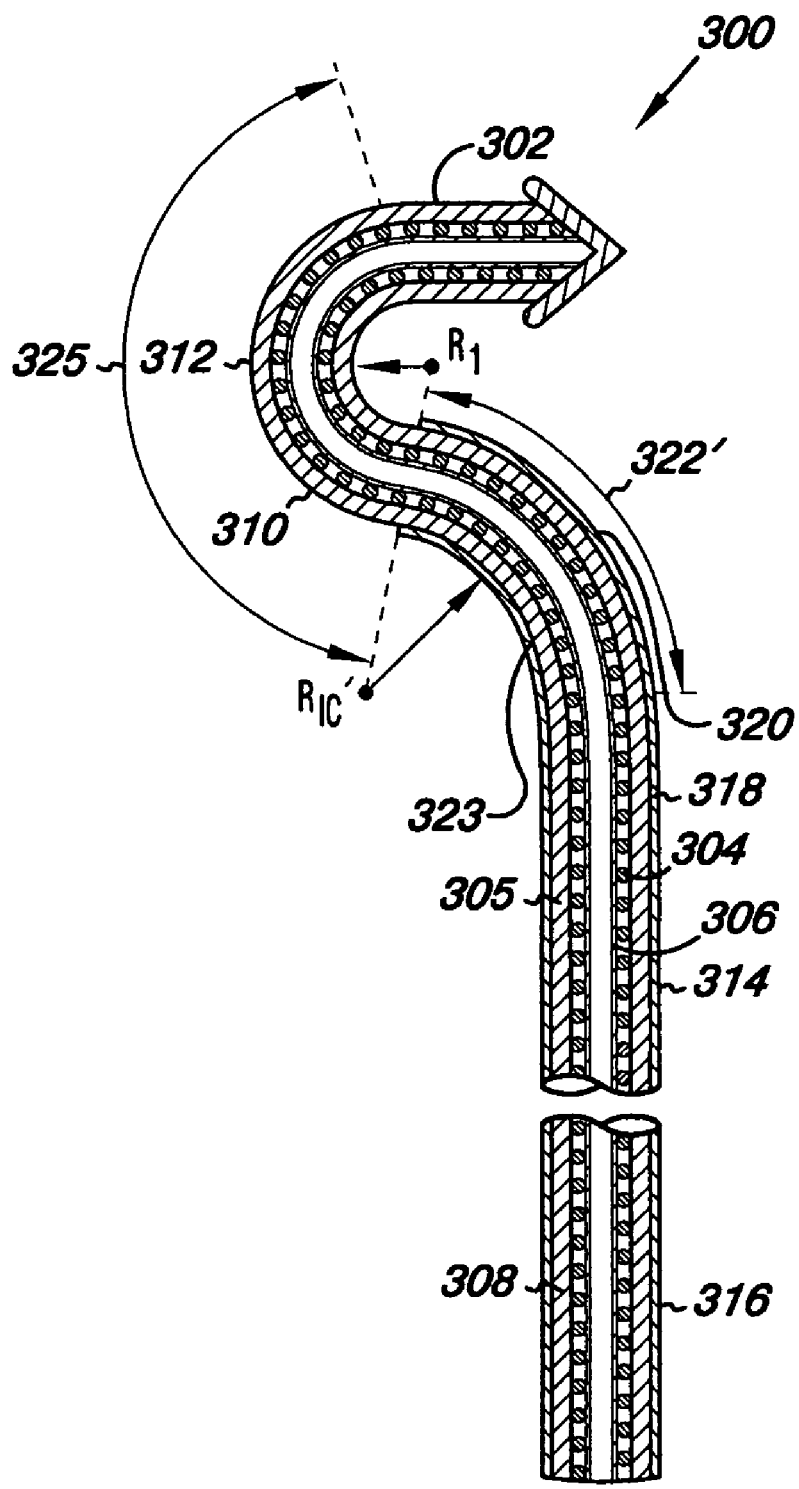
FIG. 9C is a sectional view of the pacing lead of FIG. 9A assembled with the inner catheter of FIG. 9B.

FIGS. 9A-9D show a pacing lead and inner catheter assembly 300 according to yet another embodiment of the present invention, in which a portion of the lead curvature is formed with an inner catheter. FIG. 9A shows a detailed sectional view of a pacing lead 302 in accordance with one embodiment of the present invention. Lead 302 is an elongated flexible member constructed of an inner conductive coil 304 sandwiched between an outer sheath 305 and an inner sheath 306. A proximal end 308 of the lead 302 is generally straight while a distal end 310 is pre-formed with a distal curve 312 having a radius of curvature $R_1$.

FIG. 9B shows a side view of an inner catheter 314. The inner catheter 314 is an elongated member having a central lumen 315 extending therethrough. Catheter 314 has a proximal end 316 that is generally straight and a distal end 318 provided with a pre-formed curve 320. The inner catheter 314 is sized to slidably receive the lead 302 in the lumen 315 and to be slidably received in the guide catheter lumen 26 (See FIG. 9D). According to one embodiment, the inner catheter curve 320 has a radius of curvature $R_{IC}$ of at least about twice the radius of curvature $R_1$ of the distal curve 312 of the lead 302. According to one embodiment, the radius of curvature $R_{IC}$ of the inner catheter curve 320 is from about 2 cm to about 15 cm and the radius of curvature $R_1$ of the lead distal curve 312 is from about 1 cm to about 7.5 cm. According to one embodiment, the inner catheter curve 320 extends from about 15° to about 180° relative to the proximal end 316 of the inner catheter 314, as shown by arrow 322. According to another embodiment, the inner catheter curve 320 extends about 60° relative to the proximal end 316 of the inner catheter 314.

FIG. 9C shows the pacing lead and inner catheter assembly 300. The lead 302 is inserted into the catheter lumen 315 and advanced distally. The lead 302 is positioned so that the lead distal curve 312 extends distally from the inner catheter curve 320. The inner catheter 314 is sufficiently rigid to cause the lead 302 to bend in conformity with the inner catheter curve 320. The lead 302 is thereby provided with an inner catheter-induced or proximal curve 323 in addition to the lead distal curve 312. The proximal curve 323 has a radius of curvature $R_{IC}'$ about the same as the radius of curvature $R_{IC}$ of the inner catheter curve 320. The proximal curve 323 also extends relative to the proximal portion 308 of the lead 302, as shown by arrow 322', as the inner catheter curve 320 extends with respect to the proximal end 316 of the inner catheter 314.

According to one embodiment, the lead proximal curve 323 extends from about 15° to about 180° relative to the proximal end 308 of the lead 302, as shown by arrow 322'. According to another embodiment, the proximal curve 323 extends about 60° relative to the proximal end 308 of the lead 302. According to one embodiment, the inner catheter 314 is positioned so that the lead distal curve 312 extends from about 70° to about 270° in the reverse direction as the lead proximal curve 323, as shown by arrow 325. According to another embodiment, the inner catheter 314 is positioned so that the lead distal curve 312 extends about 150° in the reverse direction as the lead proximal curve 323.

According to one embodiment, the radius of curvature $R_{IC}'$ of the lead proximal curve 323 is at least about twice the radius of curvature $R_1$ of the lead distal curve 312. According to one embodiment, the radius of curvature $R_{IC}'$ of the lead proximal curve 323 is from about 2 cm to about 15 cm and the radius of curvature $R_1$ of the lead distal curve 312 is from about 1 cm to about 7.5 cm.

FIG. 9C shows the lead distal curve 312 extending tangent to the proximal curve 323. According to other embodiments, the lead 302 is advanced distally so that the lead distal curve 312 is separated from the lead proximal curve 323 by from about 1 cm to about 2 cm.

FIG. 9C shows the lead distal curve 312 extending in the same plane as the lead proximal curve 323. However, according to other embodiments, it is contemplated that the inner catheter 314 may be positioned with respect to the lead 302 such that the lead distal curve 312 extends up to about 60° out-of-plane with respect to the lead proximal curve 323. An out-of-plane distal curve 312 would be useful for accessing vessels having unusual take-off angles.

Figure 9D:
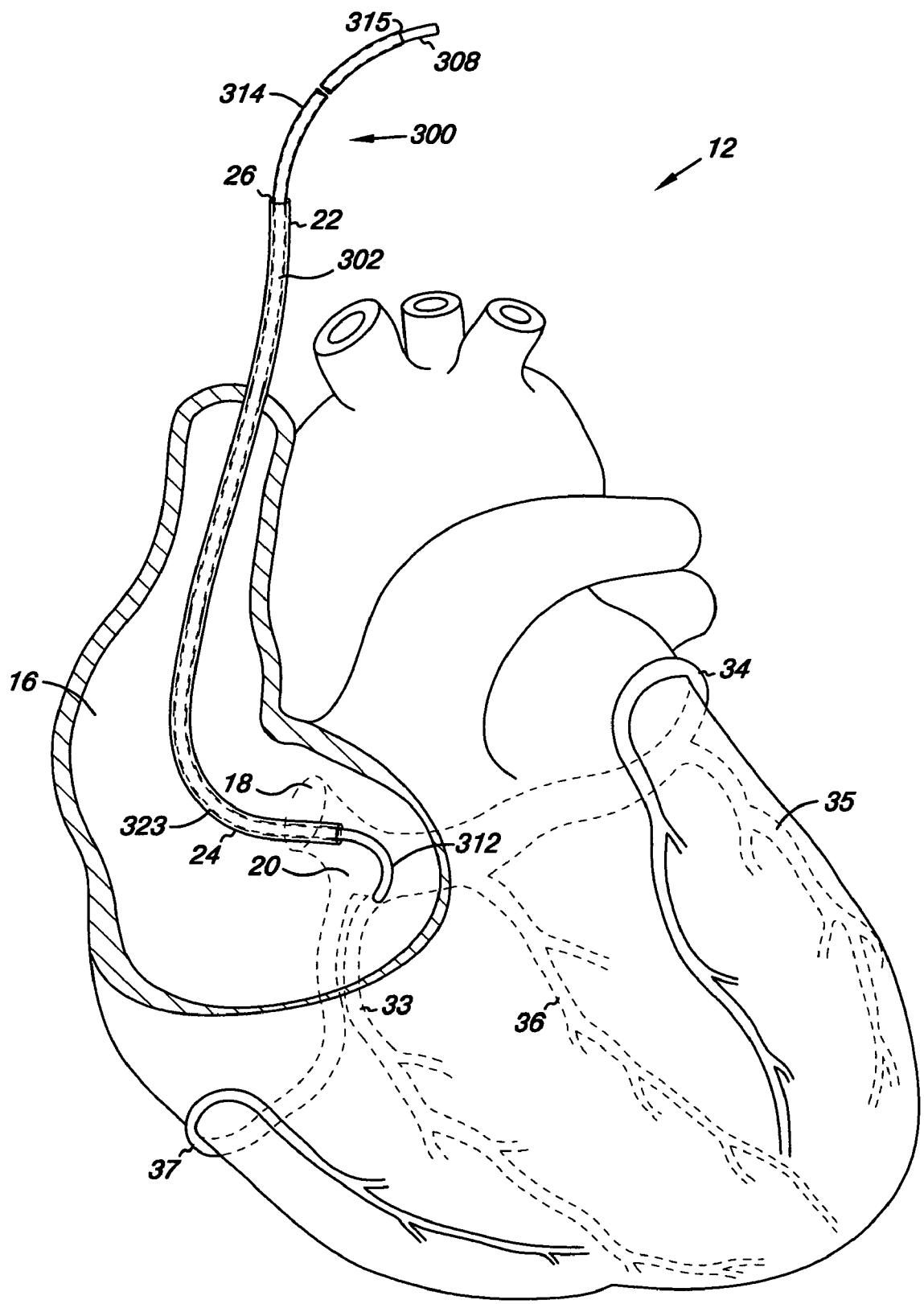
FIG. 9D is a sectional view of the pacing lead and inner catheter assembly of FIG. 9C inserted into a portion of the vasculature.

FIG. 9D shows the pacing lead and inner catheter assembly 300 of FIG. 9C and a portion of the vasculature. The lead 302 is positioned in the inner catheter lumen 315 to form the lead and inner catheter assembly 300. The lead assembly 300 is received in a guide catheter 22 as previously described. As the proximal curve 323 traverses the guide catheter curve 24, the lead assembly 300 rotates such that the lead distal curve 312 is aligned to access the middle cardiac vein 33. According to other embodiments, the lead and inner catheter assembly 300 can be employed to access any other lateral branch vein of the coronary sinus 20 as is known in the art of cardiac function management. For example, the lead and inner catheter assembly 300 can be employed to access the great cardiac vein 34, the left marginal vein 35, the left posterior ventricular vein 36 or the small cardiac vein 37.

Figure 10:
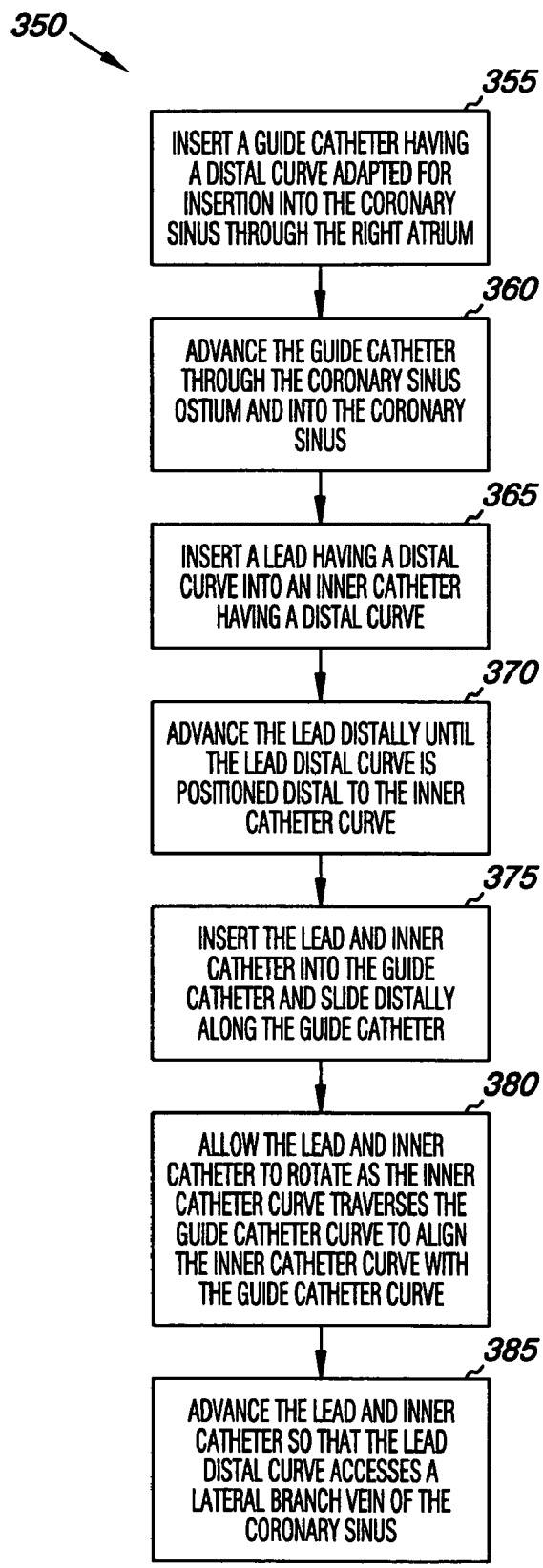
FIG. 10 is a flowchart depicting a method of accessing lateral branch veins of the coronary sinus according to one embodiment of the present invention.

FIG. 10 is a flowchart depicting a method 350 of accessing lateral branch veins of the coronary sinus according to one embodiment of the present invention. A guide catheter having a distal curve adapted for insertion into the coronary sinus is inserted in the right atrium through an access vessel (block 355). The guide catheter is advanced through the coronary sinus ostium and into the coronary sinus (block 360). A lead having a distal curve is inserted into an inner catheter having a distal curve (block 365). The lead is advanced distally until the lead distal curve is positioned distal to the inner catheter curve (block 370). The lead and inner catheter are inserted into the guide catheter and advanced distally along the guide catheter (block 375). The lead and inner catheter are allowed to rotate as the inner catheter curve traverses the guide catheter curve to align the inner catheter curve with the guide catheter curve (block 380). The lead is advanced so that the lead distal curve accesses a lateral branch of the coronary sinus (block 385).

Although the present invention has been described with reference to preferred embodiments, persons skilled in the art will recognize that changes may be made in form and detail without departing from the spirit and scope of the invention.

We claim:

1. A pacing lead and catheter assembly for accessing lateral branch veins of the coronary sinus, the pacing lead and catheter assembly comprising:
    a guide catheter having an open lumen extending therethrough, a proximal end and a distal end, said distal end pre-formed with a guide curve; and
    a chronic pacing lead having an elongated lead body, an electrode coupled to the lead body and in communication with a conductor, and a fixation mechanism coupled to the lead body, wherein the pacing lead is slidably receivable within the guide catheter lumen, and has a proximal end and a distal end pre-formed with a first curve and a second curve extending proximally from the first curve, said second curve adapted to mate with the guide curve to direct the first curve into a selected branch vein of the coronary sinus;
    wherein the lead body is non-torquable such that, during implantation, rotation of the proximal end is not transferred to the guide curve.

2. The pacing lead and catheter assembly of claim 1 wherein the first curve extends through an angle of from about 70° to about 270° in the opposite direction as the second curve.

3. The pacing lead and catheter assembly of claim 1 wherein a radius of curvature of the first curve is from about 1 cm to about 7.5 cm and a radius of curvature of the second curve is from about 2 cm to about 15 cm.

4. The pacing lead and catheter assembly of claim 1, wherein a radius of curvature of the second curve is about the same as a radius of curvature of the guide curve.

5. The pacing lead and catheter assembly of claim 1, wherein the second curve extends through a second angle of from about 15° to about 180° relative to the proximal end of the lead.

6. The pacing lead and catheter assembly of claim 1 wherein the first curve extends in a first plane and the second curve extends in a second plane, said first plane extending within about 60° of the second plane.

7. The pacing lead and catheter assembly of claim 6 wherein the first curve extends in the same plane as the second curve.

8. The pacing lead and catheter assembly of claim 1 wherein the first curve extends tangent to the second curve.

9. The pacing lead and catheter assembly of claim 1 wherein the first curve is spaced apart from the second curve a distance chosen to enhance access of the first curve into a selected branch vessel of the coronary sinus.

10. The lead and catheter assembly of claim 1 wherein the pacing lead is pre-formed with the second curve.

11. The pacing lead and catheter assembly of claim 1 wherein the second curve is formed with a stylet.

12. The pacing lead and catheter assembly of claim 1 wherein the second curve is formed with an inner catheter.

13. A pacing lead and catheter assembly for accessing lateral branch veins of the coronary sinus, the pacing lead and catheter assembly comprising:
    a guide catheter having an open lumen extending therethrough, a proximal end and a distal end, said distal end pre-formed with a guide curve;
    a chronic pacing lead having an elongated lead body, an electrode coupled to the lead body and in communication with a conductor, and a fixation mechanism coupled to the lead body, wherein the pacing lead is slidably receivable within the guide catheter lumen, said pacing lead having a proximal end and a distal end, the distal end pre-formed with a first curve extending through an angle of from about 70° to about 270°; and
    alignment means for imparting a second curve to the pacing lead corresponding to the guide curve and adapted to mate with the guide curve to direct the first curve into a selected branch vein of the coronary sinus;
    wherein the lead body is non-torquable such that, during implantation, rotation of the proximal end is not transferred to the guide curve.

14. The pacing lead and catheter assembly of claim 13 wherein the alignment means further comprises a stylet.

15. The pacing lead and catheter assembly of claim 13 wherein the alignment means further comprises an inner catheter.

16. The pacing lead and catheter assembly of claim 13 wherein the alignment means further comprises a segment of the pacing lead proximal to the first curve pre-formed with the second curve.

17. A pacing lead and catheter assembly for accessing lateral branch veins of the coronary sinus, the pacing lead and catheter assembly comprising:
    a guide catheter having an open lumen extending therethrough, a proximal end and a distal end, said distal end pre-formed with a guide curve;
    a chronic pacing lead having an elongated lead body, an electrode coupled to the lead body and in communication with a conductor, and a fixation mechanism coupled to the lead body, wherein the pacing lead is slidably receivable within the guide catheter lumen, and has a proximal end and a distal end pre-formed with a first curve and a second curve extending proximally from the first curve, said second curve adapted to mate with the guide curve to direct the first curve into a selected branch vein of the coronary sinus;

wherein the first curve extends through an angle from about 70° to about 270° in the opposite direction as the second curve;

wherein the second curve extends through a second angle of from about 15° to about 180° relative to the proximal end of the lead; and wherein the lead body is non-torquable such that, during implantation, rotation of the proximal end is not transferred to the guide curve.

18. The pacing lead and catheter assembly of claim 17 wherein the second curve has an increased stiffness relative to the remainder of the pacing lead.

19. The pacing lead and catheter assembly of claim 17 wherein at least one of the first and second curves is pre-formed by pre-loading a temporary shaped stylet in the pacing lead prior to packaging the lead.

20. The pacing lead and catheter assembly of claim 17 wherein at least one of the first and second curves is pre-formed by packaging the pacing lead in a packaging material so that the pacing lead retains at least one of the first and second curves after removal from the packaging material.

21. The pacing lead and catheter assembly of claim 17 wherein at least one of the first and second curves is heat-set to pre-form the curve.

22. The pacing lead and catheter assembly of claim 17 wherein a radius of curvature of the first curve is from about 1 cm to about 7.5 cm and a radius of curvature of the second curve is from about 2 cm to about 15 cm.

23. The pacing lead and catheter assembly of claim 17 wherein a radius of curvature of the second curve is about the same as a radius of curvature of the guide curve.

24. The pacing lead and catheter assembly of claim 17 wherein the pacing lead is pre-formed with the second curve.

* * * * *